United States Patent
Seager

(10) Patent No.: US 11,517,513 B2
(45) Date of Patent: Dec. 6, 2022

(54) NON-NANO PARTICLE SUNSCREEN COMPOSITION AND METHOD OF MAKING

(71) Applicant: Zoca Lotion LLC, Rockaway Park, NY (US)

(72) Inventor: Emily Seager, Rockaway Park, NY (US)

(73) Assignee: ZOCA LOTION LLC, Rockaway Park, NY (US)

( * ) Notice: Subject to any disclaimer, the term of this patent is extended or adjusted under 35 U.S.C. 154(b) by 0 days.

(21) Appl. No.: 17/152,921

(22) Filed: Jan. 20, 2021

(65) Prior Publication Data

US 2022/0226210 A1    Jul. 21, 2022

(51) Int. Cl.

| | |
|---|---|
| *A61K 8/27* | (2006.01) |
| *A61Q 17/04* | (2006.01) |
| *A61K 8/55* | (2006.01) |
| *A61K 8/67* | (2006.01) |
| *A61K 8/02* | (2006.01) |

(52) U.S. Cl.
CPC .............. *A61K 8/27* (2013.01); *A61K 8/0225* (2013.01); *A61K 8/553* (2013.01); *A61K 8/678* (2013.01); *A61Q 17/04* (2013.01)

(58) Field of Classification Search
CPC ....................................................... A61K 8/27
See application file for complete search history.

(56) References Cited

U.S. PATENT DOCUMENTS

2017/0189323 A1 *   7/2017  Ballenas ................ A61Q 17/04

FOREIGN PATENT DOCUMENTS

ES            2682844 A1 *  9/2018   ............ A61K 8/922

* cited by examiner

*Primary Examiner* — Benjamin J Packard
(74) *Attorney, Agent, or Firm* — Kristin Grant; Grant Attorneys at Law PLLC

(57) ABSTRACT

A environmentally and user-safe non-nano particle zinc oxide sunscreen composition that is homogenous at rest with semi-sheer to transparent application including 20 to 30% by weight of zinc oxide, 50 to 70% by weight of an oil mixture and 10 to 30% by weight of a water-resistant wax comprising beeswax, calendula wax, or a mixture thereof.

4 Claims, No Drawings

NON-NANO PARTICLE SUNSCREEN COMPOSITION AND METHOD OF MAKING

BACKGROUND

Field of Invention

The present invention relates generally to topical sunscreen compositions. More particularly, the present invention relates to topical non-nano particle mineral compositions for protection of the skin against ultraviolet (UV) rays.

Related Art

While some exposure to the sun's UV rays provides health benefits such as the production of vitamin D, too much unprotected exposure can cause skin damage, immune system suppression, and skin cancer. To avoid such negative effects, the American Academy of Dermatology recommends limiting direct sun exposure and protecting the skin with a broad-spectrum water-resistant sunscreen.

The two types of sunscreen compositions presently known are chemical compositions and mineral compositions. Chemical sunscreen compositions contain one or more UV absorbing chemical compounds such as abovenzone, octocrylene, benzophenones, salicylate, and cinnamates. While these compounds are effective in shielding the body against the sun's effects, they also pose health risks such as an increased the risk of cancer. Mineral sunscreen compositions are a healthier alternative to chemical compositions. Mineral sunscreen compositions form a layer on top of the skin and effectively scatter and reflect UVB and UVA rays. These mineral compositions commonly contain zinc oxide or titanium dioxide as their active compounds. Zinc oxide and titanium dioxide compounds are not absorbed by the skin, are not known to have any serious health effects, and are not harmful to marine-life. For these reasons, mineral compositions have been determined to be the safer option for wearers and for the environment. The zinc oxide or titanium dioxide in mineral compositions may exist in a nano particle or non-nano particle state. Nano particles are very small allowing for the creation of a homogenous sunscreen composition and a transparent application to the skin. Generally, non-nano particle compositions produce a white film on top of the skin due to the larger sized particles and exist at rest as a heterogenous mixture—this requires much mixing or shaking prior to use to blend the composition.

As a result of their size, non-nano particle compositions are safer for wearer's and for marine life as they are not easily absorbed. What is needed is an environmentally and user safe homogenous non-nano particle sunscreen composition with a semi-sheer to transparent application.

SUMMARY OF INVENTION

It is to be understood that the phraseology and terminology employed herein are for the purpose of the description and should not be regarded as limiting.

The present invention is directed to a non-nano particle mineral sunscreen composition and method of making, the composition preferably including as its active ingredient 22.5% non-nano particle zinc oxide in addition to jojoba oil, avocado oil, beeswax, shea butter, vitamin E, raspberry seed oil, carrot seed essential oil, lavender essential oil, chamomile, and calendula.

These and other features of the present invention will become readily apparent upon further review of the specification.

DETAILED DESCRIPTION

Preferred embodiments of the present invention will be described by way of example only, and not limitation. The present invention discloses a non-nano particle sunscreen composition that comprises the UV protectant zinc oxide. The sunscreen composition of the present invention further includes natural and plant ingredient& These ingredients are preferably jojoba oil, avocado oil, beeswax, shea butter, vitamin E, raspberry seed oil, carrot seed oil, lavender oil, chamomile, and calendula. However, any of these natural and plant ingredients may be substituted for an ingredient of similar qualities and characteristics.

The present invention also optionally comprises other herbs and fragrances, and other natural oils, plant extracts, water, emulsifiers, bactericides, humectins, colorants, chelating agents, anti-oxidants and foaming improvers.

Mineral sunscreen active compounds such as titanium dioxide and zinc oxide differ from chemical sunscreen active compounds in that they are not readily absorbed by the skin, but rather lie on top of the skin and prevent the UV rays from reaching the skin. The present invention comprises non-nano particle zinc oxide as its active ingredient. Zinc oxide is a well-known mineral UV blocking compound which is gentle on the skin. It is often used to treat diaper rash in infants and is a known therapeutic agent for the skin. In the present invention, titanium dioxide is nut used because titanium dioxide is widely used as a photocatalyst which generates free radicals upon exposure to sunlight. Free radicals are unstable atoms that can damage cells, causing illness and aging. Zinc oxide does not have these same properties and is as such a safer choice of active ingredient for sunscreen compositions. For these same reasons, using a combination of zinc oxide and titanium dioxide is not preferable. Further, titanium dioxide has a lower peak UVA protection than zinc oxide and is more easily worn down by chlorine which is commonly found in pools.

The present invention comprises non-nano particle zinc oxide with preferred particle sizes ranging from 0.5 to 50 micrometers. However, the present invention may be effective with no-nano zinc oxide with particle sizes of less than 100 micrometers.

A preferred embodiment of the present invention is prepared by completely melting a water-resistant wax (14%) in a steam-jacketed kettle at 150 degrees Fahrenheit. The water-resistant wax preferably being organic yellow beeswax but may also be calendula wax or similar wax commonly known in the art for its water-resistant properties.

An oil mixture (63.5%) is placed in a high shearing mixer at 2000 RPM. The oil mixture preferably comprising 37% golden organic jojoba oil, 18% virgin organic avocado oil, 3.5% raspberry seed oil, and 5% non-GMO vitamin E. The avocado oil and the jojoba oil are preferably steeped with a mixture of dried chamomile, calendula, and lavender for at least 2 weeks prior to use in order to infuse the oils with scent and for the beneficial properties of these herbs. Non-nanoparticle zinc oxide (22.5%) powder is slowly incorporated into the oil mixture while the high-shearing mixer is running at 2000 RPM. Once all of the Zinc Oxide is incorporated into the oil mixture, the zinc oxide and oil mixture combination continues to mix in the high-shearing mixer for at least 30 minutes.

The oil and zinc mixture is then added to the completely melted beeswax in the steam jacketed kettle. The steam-jacketed kettle is placed under the high shearing mixer and the oils, zinc oxide, and beeswax are mixed at 2000 RPM for 30 minutes. 20 mL of organic lavender essential oil and 10 mL of organic carrot seed essential oil are added 5 minutes before switching off the high shearing mixer.

The resulting mixture is poured into large planetary mixing bowl and allowed to cool for 8-15 hrs. The resulting mixture is then mixed using a planetary mixer for 10 minutes. The resulting mixture is run through a 3-roll mill at the finest setting twice. The present invention is then package& Homogenization is created through the use of the high shearing mixer and the three-roll mill. Such homogenization is what gives the present invention its semi-sheer to transparent quality.

The ingredient quantities provided herein are the preferred quantities however, the present invention may be effective with 20-30% zinc oxide, a 50-70% oil mixture, and 10-30% of a water-resistant wax.

This disclosure is not intended to limit the invention to the particular assembly disclosed, but, to the contrary, the intention is to cover all modifications, equivalents, and alternative falling within the scope of the claims.

What is claimed is:

1. A sunscreen composition comprising:
   (a) 20% to 30% by weight of zinc oxide, wherein the zinc oxide is in non-nano particle form;
   (b) 50 to 70% by weight of an oil mixture; and
   (c) 10 to 30% by weight of a water-resistant wax comprising beeswax, calendula wax, or a mixture thereof;
   (d) the sunscreen composition produced by:
      a. melting water-resistant wax in a steam jacketed kettle at 150 degrees Fahrenheit;
      b. placing the oil mixture in a high shearing mixer and mixing at 2000 RPM;
      c. incorporating the non-nanoparticle zinc oxide powder slowly into the oil mixture while the high-shearing mixer is running at 2000 RPM and mixing for at least 30 minutes;
      d. adding the oil and zinc oxide mixture to the melted beeswax in the steam jacketed kettle;
      e. mixing, the oil, zinc oxide and beeswax mixture in the high shear mixer at 2000 RPM for 30 minutes;
      f. adding organic lavender essential oil and organic carrot seed essential oil and mixing in the high shear mixer for an additional 5 minutes;
      g. cooling the mixture for a period of 8 to 15 hours;
      h. mixing the mixture in a planetary mixer for 10 minutes; and
      running the mixture through a 3-roll mill at the finest setting twice; and
   (e) the sunscreen composition exhibits homogeneity and a semi-sheer to transparent appearance upon application to a wearer's skin.

2. The sunscreen composition of claim 1, wherein the particles of the non-nano particle zinc oxide are 0.5 to 50 micrometers, inclusive.

3. The sunscreen composition of claim 1, wherein the oil mixture consists essentially of golden organic jojoba oil, virgin organic avocado oil, raspberry seed oil, and non-GMO vitamin E.

4. The sunscreen composition of claim 1 further comprising lavender essential oil and carrot essential oil.

* * * * *